US009494583B2

(12) United States Patent
Ko Ferrigno et al.

(10) Patent No.: US 9,494,583 B2
(45) Date of Patent: Nov. 15, 2016

(54) METHODS AND DEVICES FOR DETECTING STRUCTURAL CHANGES IN A MOLECULE MEASURING ELECTROCHEMICAL IMPEDANCE

(71) Applicants: University of Leeds, Leeds, West Yorkshire (GB); Medical Research Council, London (GB)

(72) Inventors: Paul Ko Ferrigno, Leeds (GB); Christoph Walti, Leeds (GB); David Evans, Leeds (GB); Steven Johnson, Leeds (GB); Alexander Giles Davies, Leeds (GB)

(73) Assignee: UNIVERSITY OF LEEDS, Leeds (GB)

( * ) Notice: Subject to any disclaimer, the term of this patent is extended or adjusted under 35 U.S.C. 154(b) by 0 days.

(21) Appl. No.: 13/630,391

(22) Filed: Sep. 28, 2012

(65) Prior Publication Data
US 2013/0040848 A1 Feb. 14, 2013

Related U.S. Application Data

(63) Continuation of application No. 12/440,832, filed as application No. PCT/GB2007/003465 on Sep. 13, 2007, now abandoned.

(30) Foreign Application Priority Data

Sep. 16, 2006 (GB) .................................. 0618253.9
Oct. 20, 2006 (GB) .................................. 0620808.6

(51) Int. Cl.
*G01N 33/543* (2006.01)
*B01J 19/00* (2006.01)

(52) U.S. Cl.
CPC ....... *G01N 33/5438* (2013.01); *B01J 19/0046* (2013.01); *B01J 2219/00653* (2013.01); *B01J 2219/00659* (2013.01); *B01J 2219/00704* (2013.01); *B01J 2219/00725* (2013.01)

(58) Field of Classification Search
CPC .................. B01J 2219/00653; B01J 19/0046; B01J 2219/00725; G01N 33/5438; C40B 30/04
See application file for complete search history.

(56) References Cited

U.S. PATENT DOCUMENTS

| 5,958,791 | A * | 9/1999 | Roberts et al. ............... 436/514 |
| 2002/0090649 | A1* | 7/2002 | Chan et al. ..................... 435/7.1 |
| 2003/0036054 | A1* | 2/2003 | Ladisch et al. .. G01N 33/569 11 435/5 |
| 2005/0059105 | A1* | 3/2005 | Alocilja et al. ............... 435/7.32 |
| 2006/0054511 | A1 | 3/2006 | Maurer |

FOREIGN PATENT DOCUMENTS

| WO | 01/61053 | 8/2001 |
| WO | 2004/033724 | 4/2004 |

OTHER PUBLICATIONS

Yang et al. , "Interdigitated Array Microelectrode-Based Electrochemical Impedance Immunosensor for Detection of *Escherichia coli* O157:H7", Analytical Chemistry, 2004, pp. 1107-1113.*
Navrátilová et al. , "The immunosensors for measurement of 2, 4-dichlorophenoxyacetic acid based on electrochemical impedance spectroscopy", Bioelectrochemistry (62), 2004, pp. 11-18.*
Crawford et al. , "Peptide aptamers: Tools for biology and drug delivery", Briefings in Functional Genomics and Proteomics, 2003, pp. 72-79.*
Gamry Instruments, Inc., "Basics of Electrochemical Impedance Spectroscopy", pp. 1-17; 2010.*
Li et al., "A Novel Real-Time Immunoassay Approach Utilizing an Electro-Immunosensing Microchip", Transducers '05, The 13th Conference on Solid-State Sensors, Actuators and Microsystems, 2005, pp. 1620-1623.*
K'Owino et al., "Impedance Spectroscopy: A Powerful Tool for Rapid Biomolecular Screening and Cell Culture Monitoring", Electroanalysis, 2005, p. 2101-2113.*
Hang et al., "Frequency dependent and surface characterization of DNA immobilization and hybridization", Biosensors and Bioelectronics, 2004, pp. 1537-1548.*
Karyakin et al.,"Oriented Immobilization of Antibodies onto the Gold Surfaces via Their Native Thiol Groups", Anal. Chem., 2000, pp. 3805-3811.*
Gilles et al., "Single nucleotide polymorphic discrimination by an electronic dot blot assay on semiconductor microchips", Nature Biotechnology, 1999, pp. 365-370.*
Ban et al., "Detection of protein-DNA interaction with a DNA probe: distinction between single-strand and double-strand DNA-protein interaction", Nucleic Acids Research, 2004, e110, pp. 1-8.*
Amendment/Req. Reconsideration-After Non-Final Reject in U.S. Appl. No. 12/440,832 dated Jan. 20, 2012, pp. 1-15.
Crawford et al., "Peptide aptamers: Tools for biology and drug delivery," Briefings in Functional Genomics and Proteomics, 2:72-79 (2003).
Final Rejection in U.S. Appl. No. 12/440,832 dated Mar. 30, 2012, pp. 1-17.
International Search Report in PCT/GB2007/003465 dated Jan. 2, 2008, pp. 1-3.
Kim et al., "Biosensors for label free detection based on RF and MEMS technology," Sensors and Actuators B, 119:592-599 (2006).

(Continued)

*Primary Examiner* — Lianko Garyu
(74) *Attorney, Agent, or Firm* — McAndrews, Held and Malloy

(57) ABSTRACT

The disclosure relates to a method of detecting a structural change in a molecule that is attached to a surface that is electrically conductive, wherein the method includes monitoring the phase of the electrochemical impedance at the surface, and wherein a change in the phase indicates a change in the structure of the molecule. The disclosure also relates to arrays and methods for making arrays having molecules, such as polypeptides, attached to electrically conductive surfaces, such as electrodes.

13 Claims, 6 Drawing Sheets

(56) References Cited

OTHER PUBLICATIONS

Myler et al., "Sonochemically fabricated microelectrode arrays for biosensors Part III. AC impedimetric study of aerobic and anaerobic response of alcohol oxidase within polyaniline," Biosensors and Bioelectronics, 21:666-671 (2005).

Navratilova et al., "The immunosensors for measurement of 2,4-dichlorophenoxyacetic acid based on electrochemical impedance spectroscopy," Bioelectrochemistry, 64:11-18 (2004).

Non-Final Rejection in U.S. Appl. No. 12/440,832 dated Jul. 20, 2011, pp. 1-12.

Requirement for Restriction/Election in U.S. Appl. No. 12/440,832 dated Mar. 14, 2011, pp. 1-7.

Response to Election/Restriction Filed in U.S. Appl. No. 12/440,832 dated Jun. 14, 2011, pp. 1-7.

Weber et al., "Shear mode FBARs as highly sensitive liquid biosensors," Sensors and Actuators A, 128:84-88 (2006).

Min Li, et al., A novel real-time immunoassay utilizing an electro-immunosensing microchip and gold nanoparticles for signal enhancement, Sensors and Actuators B 117 (2006) 451-456.

\* cited by examiner

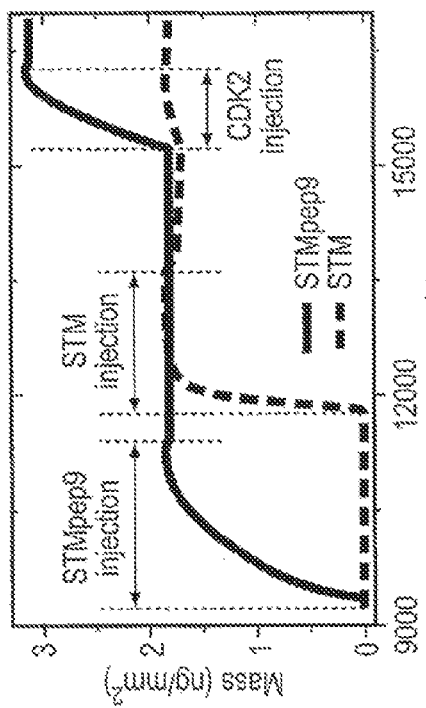
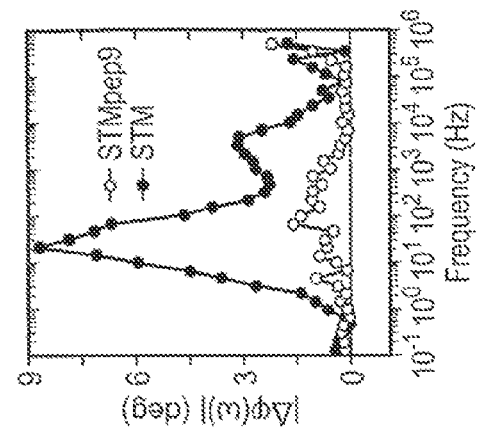
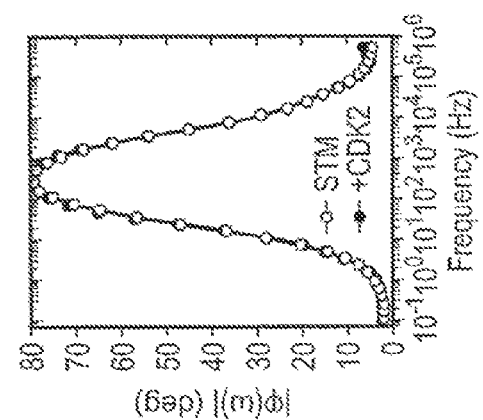
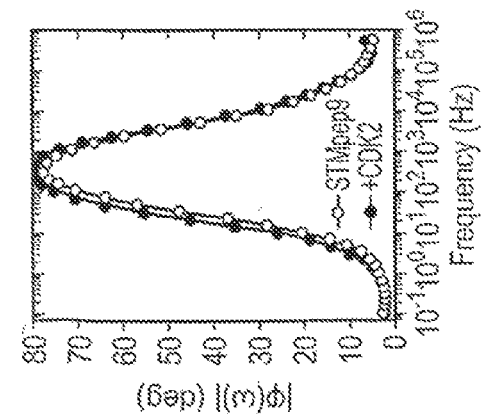
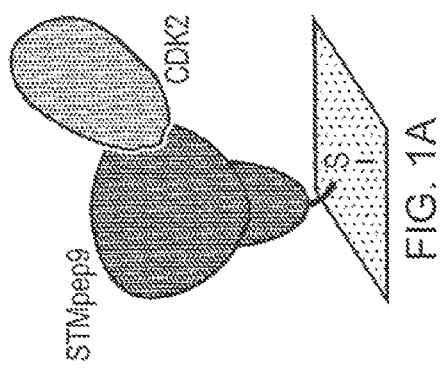
FIG. 1A
FIG. 1B
FIG. 1C
FIG. 1D
FIG. 1E

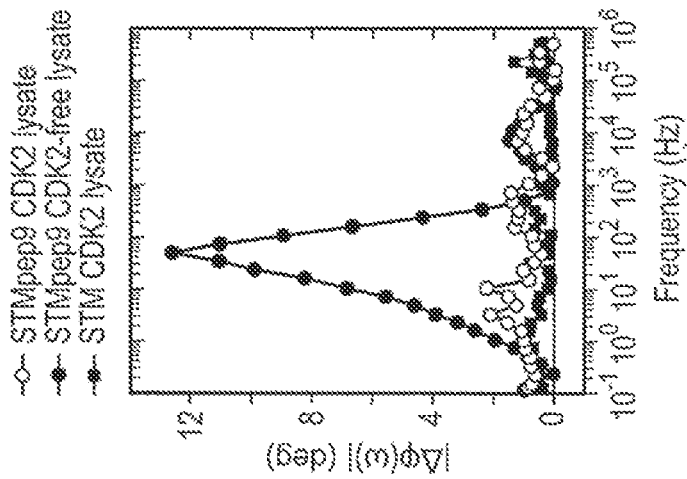
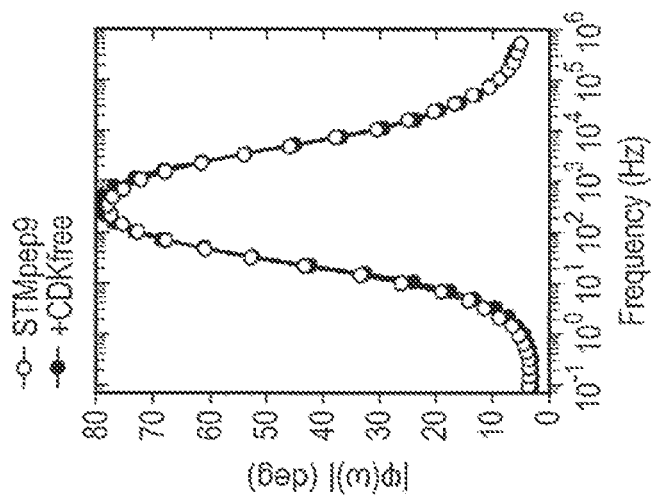
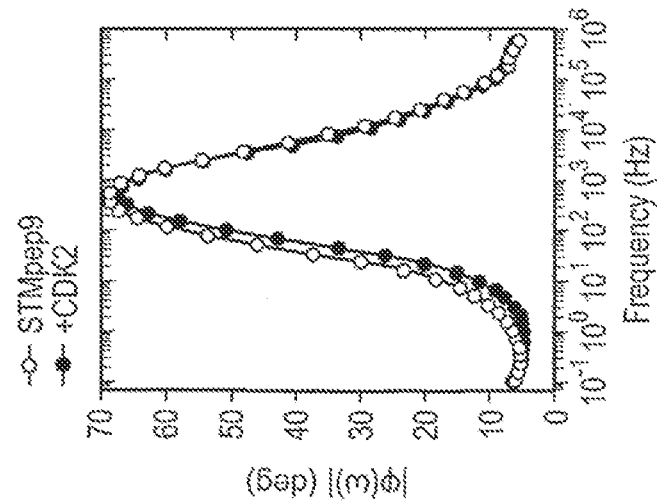
FIG. 2A
FIG. 2B
FIG. 2C

METHODS AND DEVICES FOR DETECTING STRUCTURAL CHANGES IN A MOLECULE MEASURING ELECTROCHEMICAL IMPEDANCE

The present application is a continuation application of U.S. patent application Ser. No. 12/440,832, filed Apr. 30, 2010, which is a U.S. National Phase application filed under 35 U.S.C. 371 of International Patent Application No. PCT/GB07/03465, which was filed Sep. 13, 2007, which claims the benefit of priority to British Patent Application No. 0618253.9, which was filed on Sep. 16, 2006, and British Patent Application No. 0620808.6, which was filed on Oct. 20, 2006. The entirety of all the aforementioned applications is incorporated herein by reference.

FIELD OF THE INVENTION

The present invention relates to arrays of biological molecules and their construction. The invention also relates to methods of monitoring structural changes of biological molecules, in particular conformational changes or changes in their molecular association(s).

BACKGROUND TO THE INVENTION

High-throughput, high-sensitivity detection or identification of molecules and other nanoscale objects is an important concept not only for medical diagnosis but also for drug-discovery, security, forensic and other applications. The most prominent tools for biological or chemical target detection or identification in a highly parallel fashion are microarrays. In recent years, DNA microarrays have been used extensively in genomic research, where they enabled massively-parallel interrogation of genetic code. However they are only capable of detecting or identifying complementary single stranded DNA or RNA molecules. In cases where other molecules or nanoscale complexes, for example proteins, have to be detected, more sophisticated devices, for example protein-arrays, sometimes also known in the art as protein microarrays, are required.

Protein microarrays present a significantly more difficult challenge than nucleic acid arrays, for example because of the complex nature of the proteome. Prospective protein arrays face several difficulties, in particular the identification of specific, high-affinity robust probe molecules that can bind to native proteins; the development of label-free sensing strategies for the detection of low abundance proteins in complex biological solutions; and the use of micron- or sub-micron-sized array features to enable high array densities of probe molecules.

In the art, methods of producing protein microarrays typically use surface immobilized antibodies and optical sensing of interactions with fluorescently labelled proteins. However, antibodies tend to lose their specificity and/or affinity when attached to surfaces. Further, antibodies are most often selected for binding to denatured, prokaryotically-expressed proteins either in animals or in vitro from phage display libraries. In addition, they predominantly recognize epitopes comprising conformationally constrained amino acid side chains in linear sequences. These limitations severely hinder the usefulness in applications where detection of conformationally dynamic native protein in complex bio-molecular mixtures, for example from cell lysates, is required.

Alternative probe molecules, for example RNA-aptamers, have been employed in protein arrays and these also suffer from the drawback that they usually have been selected for binding to prokaryotically expressed proteins that may not be correctly folded, and will not be post-translationally modified. The fluorescent dyes that are used to label proteins for subsequent detection of probe-target interactions are typically hydrophobic, and are likely to lead to conformational changes in labelled protein that may mask or destroy biologically relevant conformations.

A number of label-free detection strategies have been discussed in the prior art, including surface-plasmon resonance, mass spectroscopy, and atomic force microscopy-based techniques. Fabricating high-density arrays based on these strategies is however problematic and the instrumentation costs are significant.

US Patent Application No. 2005/023155 describes an apparatus and methods for the electrical detection of molecular interactions between a probe molecule and a protein or peptide target molecule, but without requiring the use of electrochemical or other reporters to obtain measurable signals. The invention described is a label-free detection system based on an electrochemical cell and conventional electrochemical impedance spectroscopy (EIS). The system is based on a glass capillary which closely resembles a conventional electrochemical cell. A problem with this approach is that array fabrication such as integrated array fabrication is extremely difficult.

International Patent Application WO2004/033724 describes a method of forming coatings of at least two different coating molecules on at least two electrodes. The method permits the preparation of nanoscale electrodes. The electrodes described therein are specifically coated using oligonucleotides and are designed for DNA and/or RNA detection. No protein or peptide based applications are demonstrated.

Prior art spotting techniques are typically available down to approximately 100 micrometers diameter of the spots of samples created. In the prior art, the smallest electrode which has previously been used has been approximately 150 micrometers in diameter. Each of these minimum size limitations represents a limitation imposed by the technical shortcomings of the state of the art.

The present invention seeks to overcome problem(s) associated with the prior art.

SUMMARY OF THE INVENTION

Electrochemical Impedance Spectroscopy (EIS) has been used for label-free detection of interactions between certain molecules in the prior art. The usual way in which this is employed is by measurement of the impedance changes which take place depending on whether molecules are bound or unbound from one another. It is these impedance measurements which represent the readout in such systems.

The present inventors have suprisingly discovered that the interactions of or conformation changes in biological molecules can actually lead to a dramatic phase shifting effect in the context of electrochemical impedance spectroscopy. Specifically, by using an alternating electrical field in an EIS type application, and by then analysing the phase shift effect, conformational changes or changes in the association between biological molecules can be very clearly detected. This is a dramatic departure from prior art techniques which have relied solely on the direct measurement of changes in impedance for their readout. The new techniques taught herein offer a number of technical benefits. One of the most important of these is that the analysis is rendered independent of the surface area of the particular probes or the particular biological molecules of interest. Thus, differences in electrode surface area or differences in electrode volumes which arise due to manufacturing tolerances or other factors are advantageously controlled for and do not confound the analysis. Furthermore, by monitoring the phase shifting as taught herein, an advantageously sensitive detection system is created.

The invention is based upon these surprising findings.

In the prior art, there is considerable interest in production of arrayed biological molecules for high-density analysis. By arraying a number of molecules of interest on a particular substrate, a very powerful analytical system can be produced. Formation of the arrays is typically performed by spotting the compounds of interest onto "pixels" or dots and thereby forming an array. Indeed, methods analagous to inkjet printing are often used in order to create the arrays of dotted analytes. However, technical limitations prevent dots being formed below certain threshold sizes. Furthermore, with regard to the spacing of the different patches, problems arise by bleeding together of neighbouring members of the array. This also constrains the overall size of the array since greater spacings are required in order to prevent cross-contamination of samples.

The present inventors have developed techniques allowing the functionalising of extremely closed spaced electrodes. Indeed, individual electrodes within an array can be differently functionalised at spacings of only a few micrometers apart. The techniques described herein are based on the controlled activation or de-protection of the individual electrodes in the array. Specifically, the present inventors have shown that an electrical field can be used to control the protection and de-protection (masking/unmasking) of individual electrodes within the array. Furthermore, they have shown that by simultaneously controlling the electrical fields surrounding neighbouring electrodes by use of further potentiostats, that "spread" effects of particular localised electric fields used in de-protection can be prevented from causing undesirable de-protection of neighbouring electrodes. Thus, advantageously extremely close spaced electrodes can be used in an array. Furthermore, the electrodes themselves can be advantageously minimised in size, further allowing a higher density of electrodes within the arrays. Thus, the present invention is based upon these novel techniques for attachment of biological molecules of interest to very small and very close spaced arrayed electrodes.

Thus, in one aspect the invention provides a method of detecting a structural change in a molecule, said molecule being attached to a surface, said surface being electrically conductive, wherein the phase of the electrochemical impedance at said surface is monitored, and wherein a change in the phase in the electrochemical impedance at said surface indicates a change in the structure of said molecule.

By structural change is meant any structural variation in the compound of interest. For example, the structural change may refer to the three-dimensional structure or conformation of the molecule. Alternatively, a structural change may refer to the binding of another entity. Such binding may be covalent or may be hydrogen bonding or may be any other kind of binding or bonding such as polymerisation or other such event. A structural change may also be considered as a modification of the molecule of interest, for example by enzymatic actions such as glycosylation, phosphorylation, de-phosphorylation or other such biologically relevant change in the chemical structure of a molecule of interest. Other examples of a structural change which might be monitored include cleavage or chopping of a molecule, for example by the action of proteases or peptidases or nucleases thereon.

Suitably the molecule is attached to the surface by a chemical bond, most suitably the molecule is attached to the surface by tethering via a thiol linkage. Alternatively, attachment to the surface may be in a sandwich or layered type arrangement. In this embodiment, a peptide may be attached to the surface via a thiol linkage. The molecule of interest may then be attached by virtue of its interaction with said first peptide. In this embodiment, chemical modification of the biological molecule of interest is advantageously avoided since the thiol group bond is mediated by the initial peptide joined directly to the electrode and the molecule of interest may then simply interact with that peptide without the need for any chemical modification thereof.

Suitably the surface comprises an electrode.

In another aspect, the invention relates to a method of making an apparatus for studying a molecule of biological interest, said method comprising providing a substrate comprising one or more electrodes wherein at least one of said electrodes further comprises a masking agent, removing said masking agent from said at least one electrode by application of an electrochemical or potential to said electrode, and attaching to said electrode a molecule of biological interest.

Suitably said apparatus comprises at least two or more electrodes, wherein during removal of said masking agent from said at least one electrode, the electrochemical potential of at least one further electrode is controlled to prevent removal of the masking agent therefrom.

Suitably said apparatus comprises an array comprising at least ten individually addressable electrodes.

In a broad aspect, the invention relates to an array comprising at least one electrically conductive electrode, said electrode having attached thereto a molecule of biological interest, said molecule comprising a polypeptide. In a preferred aspect, the invention relates to an array comprising at least two electrically conductive electrodes, at least one of said electrodes having attached thereto a molecule of biological interest, said molecule comprising a polypeptide, wherein said electrodes have one or more of:
(i) a diameter of 100 µm or less, and
(ii) a spacing of 100 µm or less.

In another aspect, the invention relates to a method of detecting a structural change in a polypeptide, said method comprising
(a) providing an array comprising at least two electrodes wherein said electrodes have one or more of:
    (i) a diameter of 100 µm or less, and
    (ii) a spacing of 100 µm or less; and
(b) attaching said polypeptide to at least one electrode of said array
(c) monitoring the electrical properties of the at least one electrode of (b), wherein a change in the electrical properties of step (c) indicates a structural change in said polypeptide. Suitably the phase of the electrochemical impedance at said surface is monitored, and wherein a change in the phase in the electrochemical impedance at said surface indicates a change in the structure of said molecule.

In another aspect, the invention relates to an array or a method as described above wherein said array comprises at least 10 individually addressable electrodes.

In another aspect, the invention relates to an array or a method as described above wherein said electrodes have one or more of:
(i) a diameter of 20 µm or less, and
(ii) a spacing of 15 µm or less.

In another aspect, the invention relates to an array or a method as described above wherein said electrodes have both (i) and (ii).

In another aspect, the invention relates to a method as described above wherein said structural change is selected from the group consisting of
(i) the binding of an entity to said molecule,
(ii) a conformational change in said molecule, and
(iii) chemical modification of said molecule.

In another aspect, the invention relates to a method or array as described above wherein the molecule comprises a polypeptide. Suitably the molecule comprises a scaffold protein. Suitably the molecule comprises a peptide aptamer. Suitably the molecule comprises a scaffold protein, said scaffold protein comprising the peptide aptamer.

Suitably said electrode comprises metal. Suitably said metal comprises gold.

In another aspect, the invention relates to a method or an array as described above wherein said molecule is a polypeptide and wherein said polypeptide is attached to said surface by a thiol linkage.

Suitably said molecule of biological interest is selected from the group consisting of aptamers, peptide aptamers, unlabelled peptide aptamers, label-free peptide aptamers, unlabelled scaffold protein comprising one or more peptide aptamers.

It should be noted that the term "functionalising" as used herein typically refers to the attaching of a molecule of biological interest to the entity being "functionalised". The molecule of biological interest is sometimes referred to herein as "probe-molecule".

It should be noted that the assembly methods or the methods of actually producing the substrate/electrode parts of the array are well known in the art. It is the techniques for selectively functionalising those electrodes which are at the heart of the present invention. The reduced diameter, and the reduced spacing, of those electrodes is a direct advantage of the particular methods of functionalising the electrodes which are disclosed herein.

Thus it can be seen that in the prior art, the large-scale spacing of electrodes is a problem. Furthermore, the bleeding together of individual compounds in the array, with technical difficulties in achieving their correct placement, and the problem of the compounds spreading following their placement are all further problems associated with the art. According to the present invention, methods for the localised and controlled individual de-protection of electrodes by the application of electric fields advantageously overcomes these problems. Furthermore, the careful control of electric fields around the neighbouring or adjacent electrodes further eliminates problems of them being affected by the procedures necessary for the de-protection and assembly of nearby electrodes.

If is a further advantage of the invention that the release of compounds from those electrodes is advantageously permitted. This may be easily implemented by the individual control of the electric fields applied to different electrodes.

PHASE SHIFT

In electronics, various electrical parameters are typically monitored by supplying a constant current and measuring the voltage, or conversely by supplying a constant voltage and measuring the current. Typically, direct current (DC) is not used, but rather oscillating (alternating or AC current) is used instead. In this way, detection is usually measured at the same frequency as the input current. The tuning or synchronisation of the detection to the same frequency to the input current is called "locking in". This is important for the elimination of noise or spurious signals. In a perfect system, the voltage and the current would oscillate or fluctuate in harmony. However, certain electrical properties such as capacitance can introduce a phase difference between the input frequency and the output frequency, whereby the peaks observed in the measured output occur with a certain time delay or lag relative to the peaks in the input. It is this phenomenon (termed 'phase lag' or 'phase shift') which is exploited in the present invention. By contrast to the prior art, the invention teaches the monitoring of the phase lag. The prior art typically deals only with the measurement of the impedance (resistance) of the system. However, the approach taught herein focuses instead on looking at the phase shift between the current and voltage observed in the systems of the invention.

It has surprisingly been shown that, as demonstrated herein, conformational changes in the molecules of interest have a pronounced effect on the phase. On a mechanistic level, it is believed that the addition (e.g. binding) of molecules onto the molecules tethered to the electrodes changes the electrode's environment though binding to, or altering the chemical nature of, the molecules attached to them; then this alters the electro-chemical properties of the electrode-solvent-external electrode assembly which is what the measurements detect, i.e. their altered dielectric properties. This can apply to characteristics such as capacitance of those electrodes. More importantly, it has now been shown that this can produce a marked phase shift in the electrical readout. Previously, those effects were not observed or not considered to have any significance since prior art techniques were based only on measurement of the impedance. Indeed, the impedance/amplitude measurements made in the prior art have been adequate outputs providing the desired readouts. It is surprising that these minor effects created by the binding of individual molecules to the electrodes produce such a pronounced phase shift effect. Furthermore, it is an advantage of the invention that such phase shift effects are independent of the surface area of the electrode involved.

It is an advantage of the invention that smaller electrode diameters may be achieved. In prior art techniques, larger sample sizes on the array were required, for example to provide sufficient signal for light based detection techniques. However, due to the sensitivity of the phase shift measurements made according in the present invention, advantageously a smaller electrode size may be used. It is an advantage of the present invention that electrode separations may be reduced. By electrode separation is meant the distance between electrodes or the gap between the nearest surfaces of neighbouring or adjacent electrodes. In the prior art, separation of the various patches or electrodes on the array had to be quite large in order to avoid complications and problems for example the bleeding together of individual samples. However, it is an advantage of the electrically controlled de-protection or unmasking of the different electrodes during manufacture of the array that such problems are advantageously avoided thereby permitting a closer electrode spacing than has been possible in the poor art.

Preferably, electrodes of the invention are no larger than 20 micrometers in diameter.

Preferably, the spacing of electrodes of the invention is no more than 15 micrometers between neighbouring or adjacent electrodes. More preferably, the spacing is 20 nanometers, more preferably the spacing is 10 nanometers, more preferably the spacing is 5 nanometers.

It is a key feature of the present invention that the molecules in the array are built up by the use of an actively controlled surface. In other words, the masking/de-protection is actively controlled by the application or suppression of electric fields around the individual electrodes being functionalised. This is in contrast to prior art techniques which are built up on inert or inactive surfaces whose properties do not change. By contrast, the present invention is based upon the construction of arrays using a dynamically changing surface, the properties of which are manipulated by the use of localised electric fields which are produced or suppressed on individual electrodes according to operator choice.

It is an advantage of the invention that quality assurance at the time of manufacture is permitted. For example, it is possible to tell the difference between a "bare" electrode and one which has been loaded with the molecule of interest. Thus, any failure in the attachment of the molecule of interest may be immediately detected before the apparatus is put into use. This advantageously helps to eliminate false negative readings when using the apparatus of the invention. One example of this may be seen in FIG. 1A.

DNA or other nucleic acids may be placed onto electrodes at close separation. Indeed, different DNA species have been placed in such close separation whilst still permitting hybridisation. However, it is an advantage of the present invention that this is now made possible for proteins. Proteins are significantly more delicate than nucleic acids in terms of their chemistry, and in terms of their capacity for chemical attachment to solid substrates. In particular, there are specific problems associated with the arraying of proteins in close separations. One of these problems is in correct attachment of proteins to the solid substrate. In addition, once attached in close vicinity denaturation or deformation of the protein can dramatically change their behaviour and prevent them from exhibiting their proper biological behaviour. However, it is an advantage of the present invention that we can produce very close spacing of immobilised polypeptides, thus avoiding problems of cross-talk or interference between those proteins which have been experienced in the prior art. This advantage is realised by the methods of manufacture (e.g. methods of functionalising electrodes with polypeptides) set out herein. This advantage is further realised by the use of scaffold proteins to constrain and correctly present the polypeptide of interest.

This is especially advantageous for embodiments of the invention featuring the use of peptide aptamers. More particularly, when the protein is a scaffold protein comprising a peptide aptamer, this acts to further constrain the peptide of interest into its most biologically relevant conformation, even when attached physically to a solid substrate such as an electrode.

Nucleic acids have typically been attached to solid substrates by the use of a short alkane chain together with a sulphur group. However, the implementation for proteins disclosed herein is different. In particular, the inventors had the realisation that it is possible to provide a sulphur group as an integral part of the protein molecule. This can be described as an alteration to permit attachment, such as a mutation or addition to the polypeptide sequence to introduce one or more thiol groups e.g. introduction of cysteine residue. This can then be exploited as the way of binding to the surface of the solid electrode. In particular, it is advantageous for the sulphur group to be provided in the polypeptide in the form of a cysteine residue. This cysteine residue can then "donate" a sulphur group for binding to an electrode surface such as a gold surface. It is surprising that this application of peptide aptamers yields special advantages. This is because the attachment of a polypeptide to a solid substrate would be expected to have an affect on the conformation of that polypeptide. However, the particular chemistry used, and especially embodiments of the invention featuring scaffold proteins immobilised onto the surface, advantageously maintain excellent polypeptide conformations even during physical attachment to the solid substrate. Thus, in a most preferred embodiment of the invention, the probe molecule or biological molecule of interest comprises a scaffold protein. More preferably, the probe molecule or biological molecule of interest comprises a scaffold protein comprising a peptide aptamer. This has the advantage of constraining the peptide aptamer and presenting it in its most biologically relevant conformation, whilst avoiding perturbation of its structure by direct attachment to the electrode; the attachment is most preferably mediated by one or more residues present in the scaffold part of a protein.

It is a particular advantage of the invention that the arrays may be operated in "label-free" mode. This advantage flows from the use of phase shift measurements in EIS detection to alleviate the need for the labelling of individual molecules in the analysis.

High throughput screening applications may be easily implemented according to the present invention. For example, it is now possible to screen for inhibitors of protein-protein interactions without the need for labelling the individual proteins involved. Clearly, once a protein is labelled its molecular structure is altered, and this can perturb or indeed obliterate the correct biologically relevant behaviour of that protein. However, it is a strength of the present invention that the individual proteins being analysed need not be modified due to the label-free phase shifted detection mechanism. Thus, it is possible to interrogate the same protein-protein interaction in multiple different molecular contexts or settings. For example, a protein of interest may be anchored to an electrode in an array according to the invention. Two such electrodes bearing the same protein may then be exposed to possible binding partners of said protein. In the controlled sample, a known binding partner would be supplied and binding would be expected to be observed. In the test samples, compounds or agents which may be candidates for the disruption or perturbation of the protein-protein interaction may be applied. In this setting, if binding is not observed in the presence of a particular compound but is observed in its absence, then that compound is identified as a candidate inhibitor of that protein-protein interaction. Similarly, screening may be conducted to find particular binding partners of a protein of interest. In this scenario, the protein of interest would be attached to one or more electrodes in the array, and possible binding partners would then be introduced to the system. By measurement of the phase shifting taking place, an indication of binding to the protein of interest is obtained. In this way, compounds capable of binding a particular protein of interest may be easily identified.

DETAILED DESCRIPTION OF THE INVENTION

It is a particular advantage of the present invention that the target or targets for all aspects of the invention can be selected from, but are not limited to, one or more of proteins, polypeptides, antibodies, nanoparticles, drugs, toxins, harmful gases, hazardous chemicals, explosives, viral particles, cells, multi-cellular organisms, cytokines and chemokines, gametocyte, organelles, lipids, nucleic acid sequences, oligosaccharides, chemical intermediates of metabolic pathways and macromolecules. Suitably the target comprises, or consists of, a biological molecule, more suitably a biological macromolecule, most suitably a polypeptide.

Throughout the description and claims of this invention, it will be understood by the person skilled in the art that proteins can be selected from one or more of, but are not limited to, native proteins, denatured proteins, protein fragments, and prokaryotically or eukaryotically expressed proteins. Suitably protein has its normal meaning in the art, most suitably 'protein' refers to a polypeptide molecule. Such polypeptide may comprise modifications such as glycosylation; phosphorylation or other such modifications as dictated by the operator.

Throughout the description and claims of this invention, it will be understood by the person skilled in the art that antibodies can be selected from one or more of the classes IgA, IgD, IgE, IgG and IgM.

Throughout the description and claims of this invention, it will be understood by the person skilled in the art that nanoparticles can be selected from, but are not limited to, one or more of insulating, metallic or semiconducting nanoparticles; nanoparticle by-products of manufacturing processes; and nanoparticles of industrial, medical, or research value.

Drugs may include those, such as, alcohol, amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, the term drugs may also include conventionally understood medicinal substances.

The invention may also involve candidate drugs, e.g. chemical entities which may be tested or screened for a particular activity or property using the arrays or methods of the invention.

Throughout the description and claims of this invention, it will be understood by the person skilled in the art that toxins can be selected from, but are not limited to, one or more toxins originating from animals, plants, or bacteria.

Throughout the description and claims of this invention, it will be understood by the person skilled in the art that viral particles can be selected from, but are not limited to, one or more viral particles with and without a genome.

Throughout the description and claims of this invention, it will be understood by the person skilled in the art that cells can be selected from, but are not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

Throughout the description and claims of this invention, it will be understood by the person skilled in the art that multi-cellular organisms can be selected from, but are not limited to, one or more of helminths, nematodes, schistosomes and trypanosomes.

Throughout the description and claims of this invention, it will be understood by the person skilled in the art that organelles can be selected from, but are not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

Throughout the description and claims of this invention, it will be understood by the person skilled in the art that lipids can be selected from, but are not limited to, one or more of signalling lipids, structural lipids, phospholipids, glycolipids and fatty acids.

Throughout the description and claims of this invention, it will be understood by the person skilled in the art that nucleic acid sequences can be selected from, but are not limited to, one or more of DNA, cDNA, RNA, rRNA, mRNA, miRNA and tRNA.

Throughout the description and claims of this invention, it will be understood by the person skilled in the art that oligosaccharides can be selected from, but are not limited to, one or more of oligosaccharides of human, animal, plant, fungal or bacterial origin.

A particular aspect of this invention is a method for the detection or identification of native proteins, and/or to detection of their conformation or their binding or association with one or more other molecule(s).

It is a particular advantage of the present invention that the probe-molecule or probe-molecules for all aspects of the invention can be selected from, but are not limited to, one or more of a biological macromolecule, an aptamer, a peptide aptamer, a recognition reagent presented in the context of another engineered protein scaffold, a DNA aptamer, a RNA aptamer, a chemical entity, a chemical entity of potential therapeutic value, a oligosaccharide, a peptide, a protein and an antibody. Suitably said molecule (probe-molecule) comprises protein or polypeptide. It is an advantage of the invention that monitoring conformation and/or molecular associations using immobilised polypeptides e.g. by monitoring phase shift (change in phase) is enabled. Furthermore, it is an advantage of the invention that attachment of polypeptides directly to small scale and/or close-spaced electrodes is enabled whereas previously such entities were typically analysed by spotting based techniques. Suitably the molecule (probe-molecule) comprises a scaffold protein, suitably said scaffold protein comprises a peptide aptamer. Attachment of polypeptides to solid phase substrates can perturb fear structure and/or behaviour. By advantageously using a scaffold protein, the peptide of interest is constrained to its desired conformation or spatial arrangement. By using a peptide aptamer within the scaffold protein, a more versatile system for presentation of the biological molecule of interest on the solid support is provided, and greater control over the proper conformation of the aptamer is afforded. Suitably attachment to the substrate/support/electrode is via the scaffold protein. This has the advantage that the peptide aptamer of interest is not directly involved in the chemical bonding to the support, thereby relieving the problem of disruption of its structure by such bonding. This has the further advantage that the peptide aptamer of interest need not be separately supplied or attached to the support, but can conveniently be attached by a universal modification of the scaffold protein, advantageously bringing consistency across different aptamers (i.e. by attachment via a common process using the scaffold protein for each different peptide aptamer) and providing the further advantage of simplification of functionalising the electrodes with different aptamers—the chemistry of attachment need not be individually designed for each different aptamer of interest but can advantageously be performed identically for each since attachment is suitably via the common scaffold, protein (rather than the individual peptide aptamer(s)).

Peptide Aptamers

Peptide aptamers are protein binding species that have been engineered to bind to various molecular targets such as small molecules, proteins, nucleic acids, or organisms and other nanoscale targets such as metal or semiconductor nanoparticles. Peptide aptamers offer utility for biotechnological and therapeutic applications as well as security and forensic applications as they offer molecular recognition properties that rival that of the commonly used biomolecule, antibodies. In addition to their discriminate recognition, peptide aptamers offer advantages over antibodies as they can be engineered completely in vitro, possess desirable storage properties, and can be designed to elicit little or no immunogenicity in therapeutic applications.

More specifically, peptide aptamers are proteins that are designed to interfere with other protein-interactions inside cells. Generally, they consist of a variable peptide loop inserted into and thus attached at both ends to a scaffold, e.g. a protein scaffold. The structural constraint imposed by the scaffold, which may be due to (1) simple restraint of the amino acid residues at either end of the inserted peptide, thus minimising freedom of movement by the remaining amino acids and their side chains and allowing them to adopt a stable configuration relative to one another, or (2) may involve conformational constraints driven by main chain or side chain interactions between amino acids of the peptide moiety and amino acids of the scaffold, or (3) a combination of (1) and (2), greatly increases the binding affinity of the peptide aptamer for its target when compared to the affinity displayed by the free peptide, to levels comparable to that of an antibody. Peptide aptamers are short peptide sequences presented and conformationally constrained in a robust, inert protein scaffold selected in vivo with high and very specific affinities for selected targets. The three-dimensional conformational constraint of the inserted peptide applied by the protein scaffold greatly increases the affinity of the aptamer for the target over that of an unconstrained peptide sequence. They are distinguished from similar protein or peptide based approaches by being selected in vivo for binding to targets from large (greater than $10^5$ unique peptide sequences) libraries using a yeast-2-hybrid approach.

Proteins play a significant role in most biological processes. Every fundamental task in the cell is ultimately governed by protein-protein interactions. A comprehensive understanding of cell biology, and hence of the molecular basis of disease, will require a thorough understanding of protein behaviour, from the conformational dynamics of individual protein molecules to a catalogue of all protein-protein interactions in a given cell under given conditions. Much attention has thus been paid to developing suitable techniques for the detection of expressed proteins. Owing to the staggering number of potential protein isoforms that can be expressed in just a single cell, ultimately, high-density arrayed systems where large numbers of proteins can be studied in parallel are required. The current dominant platform technology detects the binding of immobilised antibodies to fluorescently labelled target protein molecules. While often effective, this methodology suffers hem a number of inherent limitations.

It is a particular advantage of the present invention that we present an electronic, array-format and label-free protein detection or identification system based on peptide aptamers. The peptide aptamers are selected in viva in eukaryotic cells for their ability to recognise native protein structures.

It is a particular aspect of the present invention that the probe-molecules are immobilised on an electrode structure or an electrode array structure and thus the methods of the invention typically involve the use of an electrode structure. The electrode structure should comprise one or more electrodes. Alternatively, the electrode structure could be in an array-format (electrode array structure) comprising one or more electrodes, which are preferably individually addressable. "Individually addressable" is a term known in the art and means that each electrode of the array or electrode structure can be connected electrically to external devices on its own, i.e. without the need for connecting other electrodes of the array at the same time.

The fabrication methods of such electrode structures or electrode array structures themselves are known in the art. Preferably, the array comprises at least 10, more preferably at least 20, more preferably at least 50, more preferably at least 100, more preferably at least 1,000, more preferably at least 10,000 individually-addressable electrodes.

Although the methods of the invention are applicable to electrodes of any scale, it is particularly beneficial to arrays of small electrodes. Thus, preferably, the electrodes have a diameter (largest dimension) of not more than 50 µm, more preferably not more than 20 µm, more preferably not more than 1 µm, more preferably not more than 500 nm, more preferably not more than 200 nm, more preferably not more than 50 nm. Diameter means largest dimension since the electrodes may not always assume geometrically recognised shapes due to manufacturing tolerances or other considerations. Thus, for asymmetric or finger-shaped or other forms of electrodes, 'diameter' should be interpreted accordingly to mean 'width' or 'largest dimension', suitably the largest dimension perpendicular to the plane of protrusion from the underlying substrate (so as not to take the length as the 'largest dimension'—the diameter is a measure of width).

A particular advantage of the methods of the present invention is the fact that they can be applied to electrode structures or electrode array structures where the electrodes are closely spaced. In particular, the minimum distance (separation) between the electrodes is preferably less than 100 µm, preferably below 50 µm, more preferably below 20 µm, more preferably below 1 µm, more preferably below 200 nm and most preferably below 50 nm. Preferably, this separation applies to the minimum distance between all neighbouring electrodes.

A further particular advantage of the methods of the present invention is the fact that they can be applied to electrode structures or electrode array structures with high densities of electrodes. In particular, electrode structures or electrode array structures with electrode-densities of preferably mere than $10^4/cm^2$, more preferably of more than $10^6/cm^2$, more preferably of more than $10^8/cm^2$, more preferably of more than $10^{10}/cm^2$.

The electrodes are formed of electrically conductive material. Preferably these materials are metallic but can for instance be non-metallic such as carbon or semiconductor materials. Gold, silver, platinum, copper or aluminium, and in particular gold, are preferred.

It will be understood by the person skilled in the art that the electrodes can all be fabricated from the same material, but do not necessarily have to be all fabricated from the same material. It is possible that one or more electrodes are fabricated from one material, while one or more additional electrodes are fabricated from a different material.

It is a particular aspect of the present invention that the probe-molecule can be immobilised on the surface using a peptide-aptamer that is specific to the probe-molecule. This particular peptide-aptamer is itself immobilised on the surface through an appropriate linker, preferably a thiol-linker, and more preferably the thiol is effected through a cysteine-residue in the scaffold of the peptide-aptamer.

Scaffold Proteins

Traditionally, the *E. coli* protein thioredoxin A (TrxA) has been employed as scaffold to present the peptide aptamers.

However, many TrxA-based peptide aptamers are not expressed stably in cultured eukaryotic cells which limits their use. Recently, a new protein scaffold based on a triple mutant of human stefin A has been developed to address these problems (Woodman et al., 2005). It has been shown that this new scaffold (STM) is a versatile, biologically inert scaffold that can be used to present a large range of different peptide sequences, while the simplicity and robustness of the scaffold molecule allow the production technique to be generic for all targets. To allow the attachment of the STM scaffold to a surface in a well-controlled orientation, as well as allowing the controlled release of the scaffold in a further aspect of the present invention, the STM scaffold has been mutated further to introduce a single cysteine residue at the amino terminus to allow the attachment of the scaffold to metal electrodes via S—Au bonds. This cysteine residue is the only cysteine present in the scaffold and, in three dimensions, is located at the opposite side to the peptide insert.

To demonstrate the capabilities of our protein array devices, we employed two different peptide aptamers displayed by cysteine-modified STM with affinities for cyclin-dependent kinase 2 (CDK2) and CDK4. Both CDK2 and CDK4 belong to a group of proteins involved in the regulation of the cell cycle; they are functionally related, yet share less than 50% sequence identity. The two CDK-interacting peptide aptamers (named $STM_{pep2}$ and $STM_{pep9}$, where the subscripts pep2 and pep9 refer to two different peptide sequences) were generated by insertion of oligonucleotides encoding the CDK-interacting peptide sequence derived from the thioredoxin-based peptide aptamers of Colas et al. (Nature 380, 548-550 (1996)) into restriction sites in the open reading frame encoding the STM protein scaffold. The binding of CDK to the peptide aptamers was confirmed, in vivo and in vitro, using yeast-2-hybrid screening and fluorescence resonant energy transfer spectroscopy (FRET), respectively.

Suitably the scaffold is stefin A based such as STM.
Suitably the scaffold is thioredoxin based such as TrxA.
The peptide aptamer may have an affinity for cyclin-dependent kinase, especially where the cyclin-dependent kinase is selected from CDK2 and CDK4; the scaffold attached peptide aptamers may be selected from $STM_{pep2}$ and $STM_{pep9}$. However, it will be well understood by the person skilled in the art that the invention is not restricted to the use of these two peptide aptamers as probe-molecules; in fact the methods for the fabrication of devices to detect molecular interactions as well as the methods for the detection and the methods for the controlled release are generally applicable and hence can be used in conjunction with a wide range of probe-molecules. Furthermore, the target shall not be limited to proteins, but would also include other substance such as, inter alia, drugs, explosives, nanoparticles.

Conventional methods for fabricating protein arrays generally employ dot-printing techniques, with resolutions of around 0.1 mm. Although the resolution of these printing techniques has improved in recent years, the feature sizes required for high-density protein arrays are beyond the scope of such printing systems.

It is a particular advantage of the present invention that it enables the selective functionalisation of individual electrodes of an electrode structure or electrode array structure with dimensions smaller than those which can be achieved by conventional techniques with probe-molecules such as peptide aptamers. The resolution of the method disclosed in the present invention is only limited by the resolution of the electrode structure or the electrode array structure. Hence, for this particular method, the preferred spacing between the individual electrodes as well as the density and the diameter of the electrodes are described above. In particular, spacings of 20 nm or less, 10 nm or less, or 5 nm or even less are embraced. In some embodiments such small spacings are particularly applicable to nucleic acid applications such as functionalising the electrode(s) with DNA.

Here, selective functionalisation of the micro-electrodes with different probe-molecules aptamers is achieved through the molecular masking process illustrated in FIG. 3. The electrode structures or electrode array structures, preferably comprising multiple, individually addressable Au electrodes, are first coated with masking molecules (masking agent) which results in a masking layer that prevents non-specific binding of probe-molecules such as peptide-aptamers to the electrode structure during electrode functionalisation. The masking molecules are preferably thiol-modified to facilitate an orientation-controlled and reversible immobilization on the surface. This thiol-modification not only allows the spontaneous formation of a molecular monolayer on the Au micro-electrodes through the Au—S bond but also provides a means for removal of the masking layer from any individual micro-electrode through cleavage, preferably by electrochemical means, of the Au—S bond.

Throughout the description and claims of this invention, it will be understood by the person skilled in the art that the masking agents can be selected from but are not limited to one or more of poly(ethylene-glycol) (PEG), alkane chains, mixed alkane chains-PEG molecules, modified PEGs such as methyl-terminated PEG (mPEG), derivatised PEG, and other molecules that inhibit the adsorption of probe-molecules to the surface. It is also understood that the masking-molecules can, but do not necessarily have to be immobilised onto the surface in one step. One further possibility is to attach a molecular layer, preferably formed from thiolated molecules and attached preferably through forming gold-sulphur bonds, onto which the masking-molecules can be attached at a later stage. As an example, a layer of hydroxyl-terminated molecules can be adsorbed onto the electrodes, and at a later stage, silane-functionalised mPEG molecules can be attached to this layer.

Electrochemical cleavage of gold-thiol bonds is well known in the art. Selective removal of the masking layer from an individual micro-electrode is preferably achieved in a three-electrode electrochemical cell (comprising one or more working electrodes, one or more counter electrodes, and one or more reference electrodes) by, for example, applying an electrochemical potential of −1.4 V vs Ag/AgCl for 120 seconds using a potentiostat (FIG. 3(b)). However, other types of electrochemical cells, e.g. two-electrode electrochemical cells (comprising one or more working electrodes, and one or more counter electrodes) can be used as well. It is well understood by the person skilled in the art that electrochemical parameters depend on the environment (e.g. buffer) and hence the protocol given in the present invention is given as an example only.

Owing to the small spacing between the micro-electrodes, the electric fields generated during desorption can influence the electrochemical potential of neighbouring micro-electrodes, potentially disturbing the blocking layer. To prevent this, whilst allowing scalability to increasingly smaller micro-electrode geometries, a second potentiostat can be used to hold the neighbouring micro-electrodes' potential at, for example, −0.2 V vs Ag/AgCl during the desorption process. Having desorbed the masking layer from a set of particular electrodes, the bare micro-electrode(s) can be functionalised with the desired probe-molecule, for example a cysteine-modified peptide aptamer, by exploiting the thiol group to form a Au—S bond, for example by incubating the device in a solution containing the probe-molecule overnight in a sealed, humid environment (FIG. 3(c)). The formation of the gold-thiol bonds is well known in the art and it is understood by the person skilled in the art that the methods disclosed in the present invention shall not be limited to passive adsorption of molecules onto the surface to functionalise it. In some embodiments it is preferred to allow passive adsorption but in some embodiments it can be preferred to use active adsorption, for example by apply an electrochemical potential to the electrodes, or applying an electric field to the molecules, inter alia. This process can be repeated to functionalise further micro-electrodes with different probe-molecules (FIG. 3(d)).

An additional step may need to be introduced after each time a set of micro-electrodes of the micro-array is functionalised with a particular probe-molecule. Because this probe-molecule layer has to serve as a masking layer in any subsequent functionalisation steps, it must be able to stop other probe-molecules, to which the micro-array is exposed to during these future functionalisation steps, from attaching to this particular micro-electrode. This is not necessarily the case for all probe-molecules that may be used in conjunction with the present invention, and a regeneration step after the adsorption of the probe-molecules, may be desired after each probe-molecule functionalisation step. Such a regeneration step could, for example, comprise the exposure of the entire micro-array to appropriate masking molecules (such as mPEG-thiols (see below), preferably using the same conditions as for the generation of the initial masking layer).

An alternative way of functionalising different microelectrodes with different probe-molecules is a variation of the method discussed above. The entire micro-electrode array is first coated with the first probe-molecule (PM1) using the thiol-modification of the probe-molecule as described above (for example cysteine-modified peptide aptamers), and subsequently PM1 is released from all microelectrodes which, in the final device, should not be functionalised with this particular probe-molecule, by electrochemically breaking the S—Au bond (see above). As above, owing to the small spacing between the micro-electrodes, the electric fields generated during this desorption can influence the electrochemical potential of neighbouring, micro-electrodes, potentially disturbing the probe-molecule-layer on them. To prevent this, whilst allowing scalability to increasingly smaller micro-electrode geometries, a second potentiostat can be used to hold the potential of the electrodes that should not be desorbed, for example, at −0.2 V vs Ag/AgCl during the desorption process. In a second step, the entire micro-array is exposed to a second probe-molecule (PM2) which is adsorbed onto all electrodes that do not already contain a layer of other probe-molecules from previous steps (the probe-molecules attached to microelectrodes in previous steps serve as a masking layer for those particular electrodes and hence prevent the adsorption of further, different probe-molecules). Subsequently, PM2 is released from all electrodes which, in the final device, should not be functionalised with PM2, again by electrochemically breaking the Au—S bonds. Obviously, microelectrodes functionalised in previous steps are omitted from the electrochemical desorption process. To prevent any adverse impact owing to the desorption potentials applied to neighbouring electrodes, a second potentiostat can be used to hold these micro-electrodes' potential at, for example, −0.2 V vs Ag/AgCl during the desorption process. This process can be repeated to functionalise further microelectrodes with different probe-molecules.

As optional regeneration-step similar to the optional step discussed above can be introduced after each time the micro-array is functionalised with probe-molecules.

It is a particular advantage of the present invention that these functionalisation methods can be used for array-devices with micrometer features, as well as for array-devices with nanometer features.

Detection/Results

It is a particular advantage of the present invention that it enables the label-free electronic defection or identification of biological or chemical targets by detecting (bio)recognition events occurring between target-proteins in solution and probe-molecules immobilized on electrode structures or electrode array structures comprising one or more electrodes, preferably at a high-density. Suitably the methods of the invention comprise label-free detection. Suitably detection is based on detecting changes in one or more electrochemical (e/c) properties such as impedance. Most suitably detection is based on detecting a change in phase of the e/c impedance at one or more frequencies. Suitably the electrochemical impedance spectroscopy (EIS) measurements $|Z(\omega)|$ and $\phi(\omega)$ are determined as a function of frequency between 0.1 Hz and 500 kHz. Suitably the method may involve monitoring changes in phase of other electrical signals.

Electronic, label-free, on-chip detection of the probe-molecule-target interactions is based on monitoring local changes in the impedance of the electrochemical double layer which forms above the surface of a metal electrode when it is submerged in an electrolyte. Any perturbation of this double-layer, for instance by attachment of proteins to the electrode, alters the double-layer's electrical properties. For example, the complex electrical impedance which is determined from the response of the system, i.e. the electrochemical current $I(\omega)$, upon applying an ac electrochemical potential $\phi$ of frequency $\omega$ to the electrode, is a measure of the extent to which the charge transfer to and from the electrode is impeded by the surface-immobilized proteins. Hence $Z(\omega)$ depends on the density thickness and internal structure of the protein layer, and any alteration of this layer, tor example the binding of a molecular target, potentially results in a measurable change of $Z(\omega)$. Changes in $Z(\omega)$ manifest themselves in changes of the absolute impedance $|Z(\omega)|$ and its phase $\phi(\omega)$, i.e. the phase difference between $\phi$ and $I(\omega)$. We note that while $|Z(\omega)|$ scales with the electrode surface, $\phi(\omega)$ is independent on the electrode area, and changes in $\phi$, $\Delta\phi(\omega)$, therefore provide a reliable and reproducible measure of changes in the protein-layer properties.

A further advantage offered by the present invention is that the method of detecting target molecules is scaleable. Generally, with conventional electrochemical impedance spectroscopy (EIS) the resistance and/of capacitance is measured. However, such measurement suffers from the disadvantage that the measured quantify is proportional to the surface area of the electrode. It is a particular aspect of the present invention that, inter alia, the phase of the electrochemical impedance is surface-area-independent and hence a change of the phase owing to, for example, a binding event occurring between the probe- and the target-molecule, is surface-area-independent.

In a further aspect of the present invention we provide a method as hereinbefore described which comprises the measurement of a phase shift of the complex impedance by electrochemical impedance spectroscopy (EIS) to detect binding-events that occur between a probe-molecule and its respective target.

In most biologically relevant specimens, the proteins of interest are only present at very low abundance and in complex biological mixtures. It is a particular advantage of the present invention that proteins in such solutions can be detected or identified, even if they are only present at very low concentrations.

It is a further aspect of the present invention that the electrodes of the electrode structure or electrode array structure can be functionalised with probe-molecules that are able to detect changes in bio-molecules in biological samples from cells or organisms that have been heated with a given drug. This is particularly useful for both assessing the likely efficacy or toxicity of a drug, and also for determining whether a drug is working in a particular patient by the production of a typical signature of responsiveness.

It is a further aspect of the present invention that the probe-molecules are immobilised on a surface and in a particular aspect of the present invention, we provide a method to attach the probe-molecules reversibly to the surface, which permits the controlled release of the probe-molecules from the surface. The method is based on using a controlled-release-probe-molecule, which is a probe-molecule that has been modified with a linker-moiety to be attached reversibly to a surface. The modification with the linker-moiety of the probe-molecule can be achieved by either integrating the linker-moiety directly into the probe-molecule or by adding it to the probe-molecule via a linker. It is well understood by the person skilled in the art that the controlled-release-probe-molecule can consist of more than one part and does not necessarily has to be attached to the electrode in one step, but can equally well be assembled from its individual parts directly on the electrode. However, the preferred method is to assemble the controlled-release-probe-molecule, i.e. modifying it with a linker-moiety, first, and then immobilise it onto the surface in a subsequent step.

In a particular aspect of the present invention the controlled-release-probe-molecule is modified with a thiol, and preferably the thiol is affected through a cysteine-residue.

The S—Au-bond with which the controlled-release-probe-molecules are attached to the electrodes of the array, is electrochemically active in the same way as the thiol-Au bonds of the masking-molecules used in the selective functionalisation process. This offers the unique advantage that these bonds can be cleaved on selected electrodes only and hence the probe molecules are released back into the surrounding electrolyte (for example a protein-friendly buffer). This can obviously be done subsequent to binding a target (for example from a cell lysate), and hence the probe plus the target can be released, allowing subsequent, identification of the target by, for example, mass spectrometry.

In a particular aspect of the present invention we disclose a method for highly-parallel investigations of the differences between two or more cell types, for example between healthy and cancerous cells. A peptide-aptamer array with multiple individually addressable electrodes functionalised with different peptide aptamers may be fabricated and the response of the lysate from a cancerous cell is compared with the response of a second, identical array to the exposure to the lysate of a healthy cell. The proteins on the electrodes of the arrays where the response is different (in a positive or negative way) can be released off the electrode and the released proteins including the bound targets can be collected and analysed. Current technologies do not offer this option and the analysis of such systems may prove to be of great importance in diagnostics, the discovery of new bio-markers or drug targets, of markers of clinical efficacy of experimental treatments and in drug development, for example.

A further particular aspect of the present invention is a method for the controlled release of target molecules by electric means. Many biological molecules are known to alter their conformation quite dramatically when exposed to AC or DC electric fields. For example, surface-immobilised DNA molecules change from a random-coil-conformation to an elongated conformation when electric fields of several hundred kV/m at frequencies of around 300 kHz am applied.

This invention discloses a method for releasing the captured target-molecule off a probe-molecule immobilised on an electrode surface. It is well understood by the person skilled in the art that this electrode is not limited to be a single, isolated electrode, but can be, for example, also a set of electrodes or be part of a micro-array. The invention is described by way of example using peptide-aptamers as probe-molecules. However, it is well understood by the person skilled in the art that the invention is not restricted to peptide aptamers and can be used in conjunction with other probe-molecules as well. When an electric field is applied to a peptide-aptamer, the electric field causes a conformational change in the scaffold. This conformational change of the scaffold in turn alters the conformation of the peptide-insert of the peptide aptamer, as the three-dimensional conformation of the peptide insert is partially governed by the constraint applied by the scaffold. The affinity of the target-probe binding changes dramatically upon a conformational change of the scaffold and thus the peptide insert, and the target-molecule is released.

It is a particular advantage of the present invention that we provide an electronic, non-destructive method for a controlled release comprising an array-format device and peptide aptamers.

In a particular aspect of the present invention we disclose a method for identifying patients or pathological specimens where a particular drug binds a target molecule that is absent in a normal sample from the same patient or from another appropriate control. Electrode structures or electrode array structures are functionalised with small chemical compounds that are candidate drugs and the response to patients or pathological specimens is compared to the appropriate control. The candidate-drugs-bound-target complexes on the electrodes where the response to the specimen and the control is different (in a positive or negative way) can be released off the electrode. Hence, the controlled release candidate drug molecules immobilized on electrode structures or electrode array structures can be used to identify patients or pathological specimens where a particular drug binds a target molecule that is absent in a normal sample from the same patient or from another appropriate control. This would allow the identification of bio-molecules whose function is being affected by the drug treatment, potentially revolutionising medicinal chemistry and drug optimisation efforts.

Throughout the description and the claims of this specification, the words "comprise" and "contain" and variations of the words, for example "comprising" and "comprises", means "including but not limited to", and is not intended to (and does not) exclude other moieties, additives, components, integers or steps.

Throughout the description and the claims of this specification, the word "immobilise" variations of the word, for example "immobilising", means "attaching a moiety to a surface using a specific linker".

Throughout the description and the claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Further Applications

In another aspect, the invention relates to the fabrication of devices for detection or identification of biological or chemical targets, methods of biological or chemical target detection or identification using probe-molecules immobilised onto an electrode structure or electrode array structure, and methods for the controlled release of molecules from such devices.

In some embodiments preferably the scaffold is not STM.

In some embodiments preferably the scaffold is not TrxA.

In a yet further aspect of the invention we provide an array device for the detection or identification of a protein or multiple proteins from a single sample. We demonstrate a new approach for an electronic, high-density protein array capable of detecting proteins in complex biological mixtures at very low concentrations. Our protein array employs peptide aptamers as the probe molecules, selected in vivo with high and very specific affinities for eukaryotically-expressed proteins. Electronic transduction of biorecognition events is achieved by monitoring changes in the complex impedance characteristics of a protein film bound to a microfabricated electrode array, and we use this strategy to probe interactions between the surface-immobilized probe-proteins and target-proteins in solution. Furthermore, we demonstrate this technique using an array structure with feature-sizes an order of magnitude smaller than available with conventional protein arrays, and which can be selectively functionalised with different peptide sequences using a novel molecular mask process. The use of robust, in vivo selected peptide aptamers and the electronic nature of the label-free detection, coupled with the scalability of the electrode functionalisation and fabrication yields the potential for increasingly small detection areas and higher sensitivities.

In a broad aspect, it will be understood by the person skilled in the art that the methods as described herein for protein-arrays are applicable to other methods or devices for the detection or identification of biological or chemical targets using probe-molecules immobilised on a surface. Hence, the methods and devices of this invention shall not be limited to the detection or identification of proteins using a protein-array, but shall also be suitable for the detection or identification of targets using alternative probe-molecules.

The invention advantageously provides polypeptide sensing methods compatible with high density array formats offering increased specificity, efficiency and accuracy. Such methods advantageously embrace label free detection.

In another aspect, the invention relates to a method of biological or chemical target detection or identification which comprises the use of one or more probe-molecules immobilised onto an electrode structure comprising one or more electrodes.

The sample to be interrogated may be a complex mixture such as a biological mixture. The sample may be selected from a cell lysate, blood, serum, urine, sputum, nipple-aspirate, saliva.

It is an advantage that the invention can detect the target even when it has an abundance of less than 100 mg/ml, or less than 100 µg/ml, or less than 10 µg/ml, or less than 1 µg/ml, or less than 100 ng/ml, or less than 10 ng/ml, or less than 1 ng/ml, or less than 100 pg/ml, or less than 10 pg/ml, or less than 1 pg/ml.

The electrode structure may be an array-format electrode array structure. Suitably the electrode array structure comprises one or more individually addressable electrodes.

Suitably the array has a density of electrodes of more than $10^4/cm^2$, suitably more than $10^6/cm^2$, suitably more than $10^8/cm^2$, suitably more than $10^{10}/cm^2$.

Suitably the electrode array device consists of ten individually addressable Au electrodes.

Suitably the electrode or electrodes are submerged in an electrolyte and detection is based on changes in the environment of the electrode/electrolyte or electrodes/electrolyte interface(s).

In another aspect, the invention relates to a method of selectively functionalising individual electrodes of an electrode structure or electrode array structure with different probe molecules wherein the probe-molecule is selected from one or more of a peptide aptamer, a recognition reagent presented in the context of another engineered protein scaffold, a DNA aptamer, a RNA aptamer, a chemical entity, a chemical entity of potential therapeutic value, a oligosaccharide, a peptide, a protein, an antibody. Suitably the selectivity is produced by molecular masking. Suitably the molecular masking agent is bound reversibly to the electrodes of the electrode structure or electrode array structure. Suitably the molecular masking agent is a thiolated molecule or a thiolated complex. Suitably the molecular masking agent is or contains poly(ethylene-glycol) (PEG). Suitably the PEG is a derivatized PEG. Suitably the PEG is thiolated PEG. Suitably the PEG is methyl-terminated. Suitably the PEG is methyl-terminated poly(ethylene-glycol)$_6$-thiol.

Suitably the molecular masking agent is or contains an alkane chain. Suitably the alkane chain is thiolated. Suitably the masking agent may be a complex composed of two or more molecules; in this embodiment suitably one of the molecules of the complex is a thiolated molecule and the other(s) are linked to this one; in this embodiment suitably the thiolated molecule of the complex is attached to the surface first, and the others are attached subsequently to the surface-bound thiolated molecule.

The molecular mask may be released from the electrode by applying an electronic signal to the electrode, for example by electrochemical cleavage of a thiol-linkage. Thereby, an electrode neighbouring the electrode that binds the molecular masking agent to be released is protected by keeping its potential at a level where the induced release-reaction does not happen. Typically an electrochemical potential of between −0.9 V and −4.5 V vs Ag/AgCl is applied to achieve this.

The electrode may be any conductive material such as carbon or metal. The metal of the metal electrode(s) is suitably selected from gold, silver, platinum, palladium, titanium, nickel and copper.

A redox-probe may be used such as a $K_3Fe(CN)_6^{4-/3-}$ redox probe. The electrolyte may consist of a buffer and a redox-probe.

In another aspect, the invention relates to an array format system for biological or chemical target detection or identification which comprises the use of one or more probe-molecules immobilised onto an electrode structure comprising one or more electrodes.

In another aspect, the invention relates to a method of target detection or identification which comprises the measurement of a phase shift of the electrochemical impedance and the use of an in vivo selected peptide aptamer.

In another aspect, the invention relates to a method to release a captured target which comprises the use of one or more probe-molecules immobilised onto an electrode structure comprising one or more electrodes or onto an electrode array structure comprising one or more electrodes.

In another aspect, the invention relates to a method to release a captured-target-probe-molecule complex which comprises the use of one or more probe-molecules immobilised onto an electrode structure comprising one or more electrodes.

The release method may comprise induction of a conformational change of the probe-molecule or the target. The release method may involve an electrostatic repulsion or attraction between the probe-molecule and the target. The release method involves a redox-reaction in the probe-molecule or target. The release method may involve photo-cleavage of one or more chemical bonds of the surface-probe-molecule linkage or in the probe-molecule.

The invention will now be described by way of example with reference to the accompanying drawings. These examples are intended to be illustrative and are not intended to limit the invention as defined in the appended claims.

BRIEF DESCRIPTION OF THE FIGURES

FIG. 1(a) is a schematic diagram of $STM_{pep9}$-CDK2 complex immobilised on a gold surface via conjugation between the cysteine residue (S group) and Au;

FIG. 1(b) shows the real-time increase in mass following immobilisation of $STM_{pep9}$ and STM on two, independent maleimide functionalised waveguides and following subsequent exposure to recombinant CDK2;

FIG. 1(c) illustrates EIS $\phi(\omega)$ data for an Au surface functionalised with $STM_{pep9}$ and following exposure to recombinant CDK2;

FIG. 1(d) is the same as FIG. 1(c) but following exposure of STM to recombinant CDK2; and FIG. 1(e) illustrates the change in $\phi(\omega)$ of $STM_{pep9}$ and STM layer formed on two, independent Au electrodes following exposure to recombinant CDK2.

FIG. 2(a) illustrates EIS $\phi(\omega)$ data for an Au surface functionalised with $STM_{pep9}$ and following exposure to CDK2-expressing yeast lysate;

FIG. 2(b) is the same as FIG. 2(a) but following exposure of $STM_{pep9}$ to a CDK-free yeast lysate; and FIG. 2(c) illustrates $\Delta\phi(\omega)$ of $STM_{pep9}$ formed on independent electrodes following exposure to a CDK2-expressing yeast lysate and a CDK2-free lysate and $\Delta\phi(\omega)$ of STM layer following exposure to CDK2-expressing yeast lysate.

FIG. 3(a) all electrodes are initially protected from functionalisation by a protein-inhibiting mPEG monolayer;

FIG. 3(b) the molecular mask can be released by electrochemical means;

FIG. 3(c) the bare Au micro-electrode surface is subsequently functionalised with the required protein;

FIG. 3(d) by repeating this cycle it is possible to functionalise independently multiple electrodes within a single device; and FIG. 3(e) the formation of a protein-protein complex occurring following exposure to a complex biological solution, results in a measurable shift in $\phi(\omega)$ (central electrode).

EXAMPLE 1

Figure 2D:
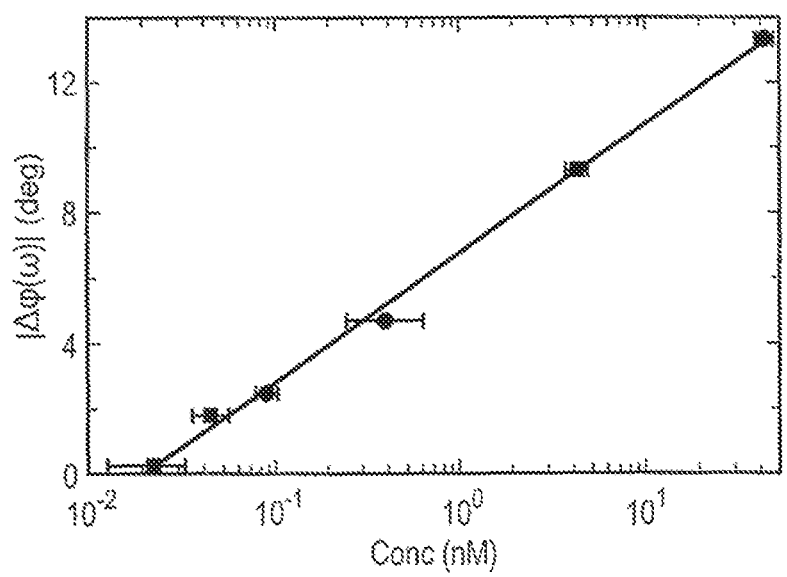
FIG. 2(d) shows rise concentration dependence of the phase shift at 70 Hz, line fitted to y=3.9340 log x+6.684.

Two different peptide aptamers were employed displayed by cysteine-modified STM with affinities for cyclin-dependent kinase 2 (CDK2) and CDK4. Both CDK2 and CDK4 belong to a group of proteins involved in the regulation of the cell cycle; they are functionally related, yet share less than 50% sequence identity. The two CDK-interacting peptide aptamers (named $STM_{pep2}$ and $STM_{pep9}$, where the subscripts pep2 and pep9 refer to two different peptide sequences) were generated by insertion of oligonucleotides encoding the CDK-interacting peptide sequence derived from the thioredoxin-based peptide aptamers of Colas et al. into restriction sites in the open reading frame encoding the STM protein scaffold. The binding of CDK to the peptide aptamers was confirmed, in vivo and in vitro, using yeast-2-hybrid screening and fluorescence resonant energy transfer spectroscopy (FRET), respectively.

Although the peptide-insert region is predicted to be far from the surface when the STM-scaffold is bound to the electrode via the cysteine-residue, we confirmed that there is no adverse impact on the performance of the peptide aptamer caused by surface-protein interactions.

The binding and functionality of surface immobilised $STM_{pep9}$ was initially characterised using dual polarisation interferometry (DPI). Briefly, DPI is a method for characterising thin molecular films, based on the detection of interference patterns resulting from coherent laser light propagating along two independent optical waveguides. Interaction of the evanescent wave with a molecular layer attached directly onto one of the waveguides influences propagation through that waveguide resulting in a shift in the observed interference pattern. By detecting these changes at two different optical polarisations, sub-Ångstrom thickness-changes in layers as well as mass-changes of sub-pg/mm$^2$ can be detected.

Experiments were performed using a Farfield AnaLight Bio200. All experiments and samples were prepared in PBS pH 7. Immobilisation of the cysteine modified protein onto the silicon oxynitride waveguide surface was achieved using a homobifunctional maleimide crosslinker for conjugation between the cysteine and sulfhydryl groups on a thiol-functionalised waveguide surface.

Following immobilisation, the $STM_{pep9}$ layer was exposed to 150 μl of recombinant purified CDK2 (30 μg/ml in PBS) expressed in *E. coli*. To confirm specific binding between $STM_{pep9}$ and the CDK2, a second waveguide functionalised with cysteine modified STM protein but without any peptide aptamer insert was simultaneously exposed to recombinant CDK2.

FIG. 1(b) shows the real-time increase in mass resulting from immobilisation of $STM_{pep9}$ and STM on the two maleimide functionalised waveguides, and following subsequent exposure to CDK2. While the mass of immobilised material is similar for both $STM_{pep9}$ and STM, only the $STM_{pep9}$ functionalised waveguide displayed a significant increase in mass upon exposure to CDK2. These results demonstrate the STM-based peptide aptamers modified with a cysteine group and immobilized on the surface using this cysteine modification, is still functional and can be used in an array-like environment.

Measurements on the same peptide aptamers-CDK2 system were carried out on a chip-based device using Electrochemical impedance spectroscopy (EIS). EIS measurements, where $|Z(\omega)|$ and $\phi(\omega)$ are determined as a function of frequency between 0.1 Hz and 500 kHz, were performed using a custom built three-electrode electrochemical cell (Pt common, Au working, and Ag/AgCl reference-electrode), and a Princeton Applied Research VSP bipotentiostat/impedance spectrometer in a common-electrode to ground configuration. The electrolyte consisted of 100 mM phosphate buffer pH 7.7 containing 10 mM $K_3Fe(CN)_6^{4-/3-}$ redox probe. All electrochemical potentials are reported against an Ag/AgCl reference electrode. The gold working-electrodes were functionalised with peptide aptamers (here either $STM_{pep9}$ or STM) by exposure of the electrode to 35 μl of protein in a PBS buffer pH 7 for 18 hours at room temperature. The devices were subsequently exposed to 45 μl of a solution containing about 200 ng/μl recombinant, purified CDK2 expressed in E. coli. Following exposure, the devices were rinsed with deionised water (18.2 Ωcm, Millipore) to remove any excess CDK2.

FIGS. 1(c) and (d) show the measured phase of the complex impedance, $\phi$, for $STM_{pep9}$ and STM, respectively, both before and after exposing the system to recombinant CDK2. A shift in $\phi$ is observed upon CDK2 binding to $STM_{pep9}$, while no change was detected in the case of STM. This shift is more obvious when plotting the difference in the phase, $\Delta\phi$, before and after exposure to CDK2 (FIG. 1(e)). While no change in $\phi$ is observed for STM, a pronounced peak is measured for $STM_{pep9}$. These results demonstrate that a change in phase provides a useful means to detect binding of the targets to the probe molecules.

EXAMPLE 2

In order to assess the suitability of our sensing strategy for the detection of proteins in biologically relevant specimens, in which the proteins of interest are only present at very low abundance and in complex mixtures, we prepared Au electrodes functionalised with $STM_{pep9}$ and STM. These were then exposed to 35 μl of a solution containing a mixture of cell products, including CDK2, generated by lysis (dissolution) of CDK2-expressing yeast cells. The use of a lysate not only allows us to confirm the specificity of the $STM_{pep9}$ aptamer for binding of CDK2, but also allows us to assess our sensing device using a complex biological sample which closely resembles those used in typical medical diagnostics. Following exposure to yeast lysate, the devices were thoroughly washed in order to remove any non-specifically bound material.

The phases $\phi$ of the complex impedances measured for the different devices are shown in FIG. 2. While a distinct shift in $\phi(\omega)$ is observed between 1 and $10^3$ Hz for $STM_{pep9}$ exposed to CDK2 lysate (FIG. 2(a)), the phase for STM exposed to the lysate does not change across the whole frequency range investigated. Again, this phase-shift can be seen more clearly in FIG. 2(c) which plots the absolute change in phase following exposure of the $STM_{pep9}$ and STM functionalised electrode to the CDK2-expressing yeast lysate. The magnitude of $\Delta\phi$ for the $STM_{pep9}$-CDK2 lysate reaches a maximum of about 12° at a drive frequency of 300 Hz. Given that $STM_{pep9}$ and STM differ only in the presence (absence) of the peptide aptamer insert, the dramatic variance in impedance characteristics following exposure to the CDK2 must be related to an interaction with $STM_{pep9}$ through the aptamer region (i.e. peptide insert). In order to confirm that this interaction is related to the formation of the CDK2-$STM_{pep9}$ complex, rather than to binding with other species contained within the lysate, we exposed a series of $STM_{pep9}$ functionalised electrodes to a lysate generated from identical yeast cells, but lacking the expression of CDK2 (FIG. 2(b)). The absence of a shift in phase following exposure to this CDK2-free yeast lysate (see FIG. 2(c)), confirms the affinity of the $STM_{pep9}$ for CDK2, in agreement with the DPI data. Bait proteins such as CDK2 are typically expressed at around $10^2$-$10^4$ molecules per cell, giving an estimated maximum concentration of CDK2 in the yeast lysate of 15 ng/ml (440 pM), which is in the clinically relevant range. Low concentration of the target protein and highly contaminated samples are typical of many biological specimens and these results demonstrate the ability of our sensor to detect unambiguously target-aptamer binding from such samples.

EXAMPLE 3

Electrode array devices consisting of ten individually addressable Au micro-electrodes separated by 15 μm, were fabricated on n-doped silicon <100> substrates capped with a 500 nm thermal oxide using a bi-layer resist process. The electrodes were of 20 μm width. Following fabrication, each device was mounted in a header package and wire bonded to provide electrical connection to each micro-electrode. To demonstrate the suitability of our technique for array format sensing, we functionalised different closely-spaced electrodes of the array with two different peptide aptamers, $STM_{pep9}$ and $STM_{pep2}$.

Figure 3:
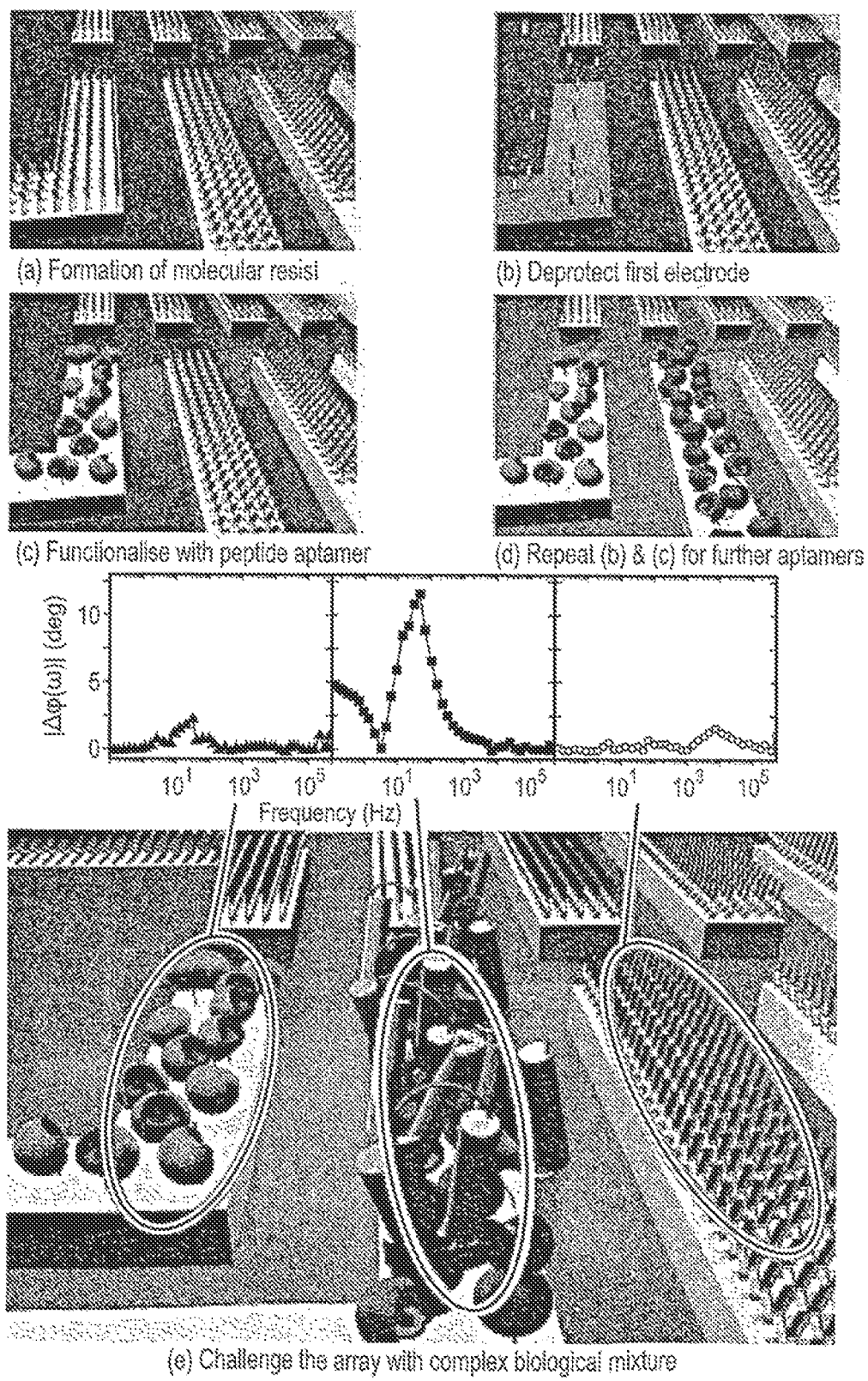
FIG. 3 is a set of schematic diagrams showing the use of a molecular mask for selective functionalisation of a micro-electrode array.

Selective functionalisation of the micro-electrodes was achieved through a molecular masking process illustrated in FIG. 3. Following the fabrication of the electrode arrays, the devices were immersed in a 10 mM methyl-terminated poly(ethlyene-glycol)$_6$-thiol (mPEG, Polypure, Norway) ethanolic solution for 96 hours (FIG. 3(a)). This mPEG layer prevents non-specific binding of proteins during electrode functionalisation. The thiol-modification of the mPEG not only allows the spontaneous formation of a molecular monolayer on the Au micro-electrode through the Au—S bond but also provides a means for removal of the masking layer from a single individual electrode through reductive cleavage of the Au—S bond. The quality of the resulting mPEG layers were verified using water contact-angle measurements and X-ray photo-electron spectroscopy, and the effectiveness of protein-inhibition was confirmed by fluorescence spectroscopy. After formation of the mPEG layer, the chips were soaked for 1 hr in deionised water to remove residual ethanol and form a water layer around the PEG, believed to be crucial, to inhibiting protein binding.

Selective reductive removal of the mPEG molecular mask from an individual electrode was performed by applying an electrochemical potential of −1.4 V vs Ag/AgCl for 120 seconds using a bipotentiostat and identical buffer conditions to those used in EIS measurements (FIG. 3(b)). Owing to the small spacing between the micro-electrodes, the electric fields generated during desorption can influence the electrochemical potential of neighbouring electrodes, potentially disturbing the blocking layer. In order to prevent this, whilst allowing scalability to increasingly small micro-electrode geometries, a second potentiostat was used to hold the neighboring electrodes' potential at −0.2 V vs Ag/AgCl during the desorption process. The efficacy of the desorption is monitored with cyclic voltammetry (see FIG. 4 (a)). Following desorption, the peak separation on the voltammogram is seen to decrease from 425 mV to 100 mV, typical of a Au surface with this redox probe. Having desorbed the mPEG molecular mask, the bare Au micro-electrode can be functionalised with the desired protein by incubating the device in 35 μl of protein solution overnight in a sealed, humid environment (FIG. 3(c)). The adsorption of the protein, and the effectiveness of the mPEG monolayers for masking deposition on protected micro-electrodes is confirmed using cyclic voltammetry and EIS. This process has been repeated to functionalise a second electrode with a different protein (FIG. 3(d)).

Figure 4A:
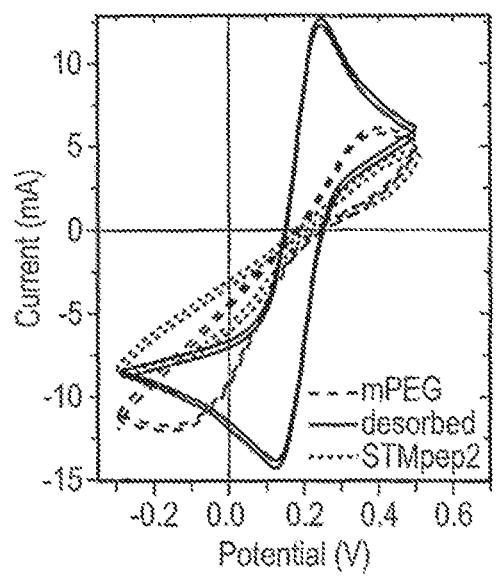
FIG. 4(a) is a cyclic voltammogram of an individual micro-electrode protected with mPEG inhibiting layer, following electrochemical desorption of the mPEG monolayer and after functionalisation with peptide aptamer $STM_{pep2}$.
Figure 4B:
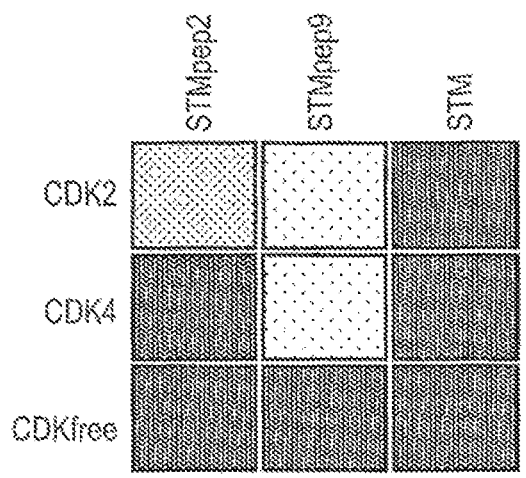
FIG. 4(b) is a FRET analysis of $STM_{pep2}$, $STM_{pep9}$ and STM upon exposure to CDK2, CDK4 and CDK-free lysate.
Figure 4C:
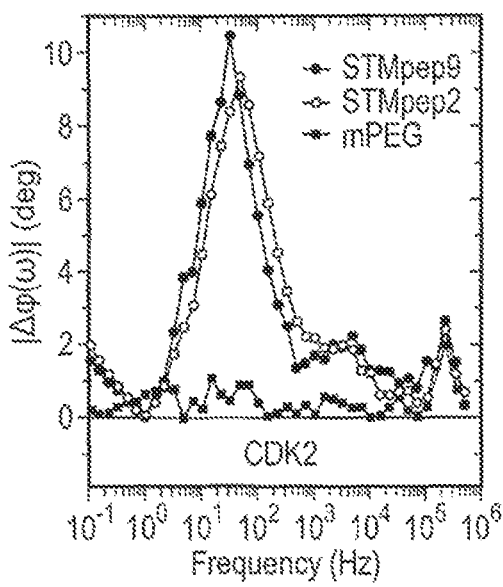
FIG. 4(c) $\Delta\phi(\omega)$ of the complex impedance for mPEG-, $STM_{pep2}$- and $STM_{pep9}$-functionalised micro-electrodes following exposure to a lysate containing CDK2.
Figure 4D:
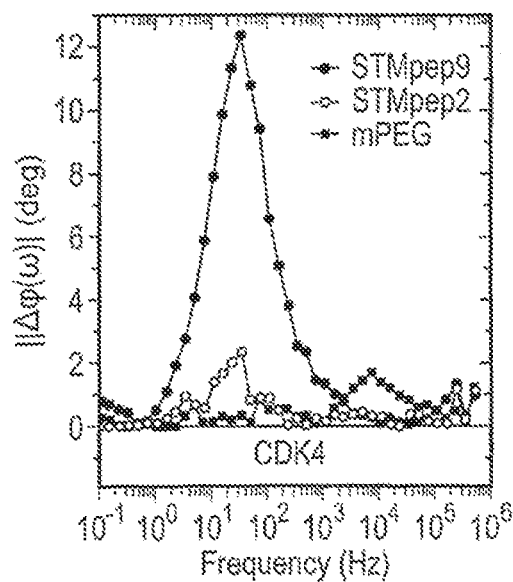
FIG. 4(d) is the same as FIG. 4(c) but following exposure to cell lysate containing CDK4.

FRET analysis confirmed that both $STM_{pep9}$ and $STM_{pep2}$ show an affinity for CDK2, while only $STM_{pep9}$ showed an affinity for CDK4 (see FIG. 4(b)). We exploit this difference in functionality to demonstrate the sensor's ability to discriminate between binding events occurring on differently functionalised micro-electrodes, fabricated on a single device, and thus we functionalised individual electrodes of the arrays with the two different peptide aptamers, $STM_{pep9}$ and $STM_{pep2}$. To demonstrate the capabilities of our array device, two separate, nominally identical devices were fabricated and functionalised, and challenged with CDK2- and CDK4-expressing lysate (containing less than 15 ng/ml CDK), respectively. The EIS results of this study are shown in FIGS. 4(c) and (d). Shifts in $\phi(\omega)$ are observed for both the $STM_{pep9}$ and $STM_{pep2}$ functionalised micro-electrodes following exposure to the CDK2-expressing yeast lysate. Conversely, upon exposure to CDK4-expressing yeast lysate, a shift in $\phi$ of similar magnitude was only observed for the $STM_{pep9}$ functionalised micro-electrodes.

These results demonstrate that we can successfully functionalise individual, μm-spaced electrodes within an array with individual proteins, and that our electronic, label-free detection method can successfully detect proteins of very low concentrations. Further, the clear shifts in $\phi$ indicate the formation of CDK2/CDK4-$STM_{pep9}$ and CDK2-$STM_{pep2}$ complexes, in agreement with FRET analysis. The lack of response following exposure of $STM_{pep2}$ functionalised micro-electrodes to CDK4 indicates the high selectivity of the functionalisation process. In all cases, $\phi$ remained constant for those micro-electrodes which remained covered with mPEG, confirming the efficacy of the mPEG inhibiting layer.

EXAMPLE 4

In order to determine the concentration dependence of the phase shift, $\Delta\phi(c)$, gold electrodes were functionalised with $STM_{pep9}$ and were exposed to 50 μl of phosphate buffer containing various concentrations of purified, baculoviral CDK2 between 25 pM and 100 nM. The electrodes were subsequently rinsed in phosphate buffer to remove any excess CDK2 before $\phi(\omega)$ was measured. The results are shown in FIG. 2(d) from where a sensitivity limit of this setup of around 50 pM (≈1.5 ng/ml CDK2) can be determined, which is in the clinically relevant range. The phase shift is linear on a logarithmic concentration scale over at least orders of magnitude. The solid line in FIG. 2(d) represents a linear fit to the data.

EXAMPLE 5

Figure 5:
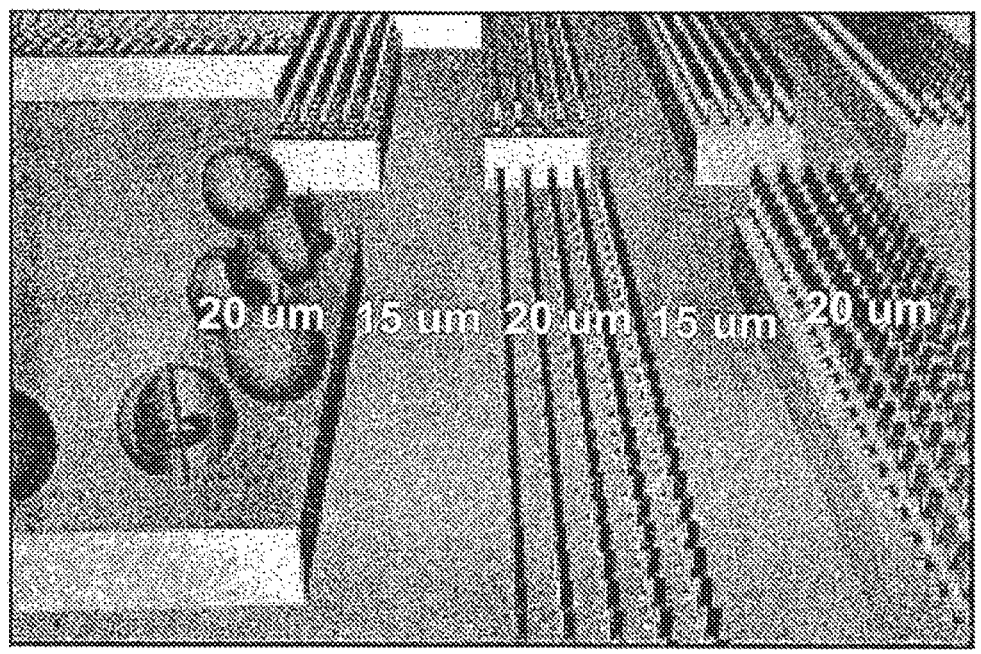
FIG. 5 shows a diagram.

An exemplary arrangement that we have demonstrated with advantageously small features comprises 10 metal electrodes, divided into two sets of five. Each electrode is of width 20 microns with a separation between adjacent electrodes, both in the x and y directions in the plane, of 15 microns. The electrodes are finger-shaped (see FIG. 5, which shows part of the array of 10 electrodes) and are not round, so the 'diameter' means largest dimension perpendicular to the plane of protrusion. The electrodes are extended over the substrate surface in order to make electrical contact from the exterior.

In another embodiment the electrodes may be brought up vertically up through the surface to produce a 2D array of pixels in the plane of the surface.

The invention claimed is:
1. A method of detecting binding of an entity to a molecule, said molecule being attached to a surface, said surface being electrically conductive, wherein the method comprises
monitoring the phase of the electrochemical impedance at said surface over a range of frequencies; and
detecting change in the monitored phase of the electrochemical impedance at said surface over said range of frequencies,
wherein said change in the monitored phase is dependent on the concentration of said entity and said change indicates said binding to said molecule.
2. The method according to claim 1, wherein said range of frequencies is a range of frequencies between 0.1 Hz and 500 kHz.
3. The method according to claim 1, wherein the surface comprises an electrode.
4. The method according to claim 3, wherein said electrode comprises metal.
5. The method according to claim 1, wherein the molecule comprises a polypeptide.
6. The method according to claim 5, wherein said method further comprises;
(a) providing an array comprising at least two electrodes, wherein each of said electrodes have one or more of (i) a diameter of 100 μm or less; and (ii) a spacing of 100 μm or less; and
(b) attaching said polypeptide to at least one electrode of said array which thereby forms said surface.
7. The method according to claim 6, wherein said array comprises at least 10 individually addressable electrodes.
8. The method according to claim 6, wherein each of said electrodes have one or more of; (i) a diameter of 20 μm or less, and (ii) a spacing of 15 μm or less.
9. The method according to claim 6, wherein said electrodes have both (i) and (ii).
10. The method according to claim 5, wherein said polypeptide comprises a scaffold protein.
11. The method according to claim 5, wherein the polypeptide comprises a peptide aptamer.
12. The method according to claim 5, wherein said polypeptide is attached to said surface by a thiol linkage.
13. The method according to claim 1, wherein the molecule comprises DNA or a nucleic acid other than DNA.

* * * * *